United States Patent [19]

Curl

[11] Patent Number: 4,529,318

[45] Date of Patent: Jul. 16, 1985

[54] METHOD AND APPARATUS FOR INSPECTING SHEETS FOR FLAWS

[75] Inventor: Barry J. Curl, Southampton, England

[73] Assignee: De La Rue Systems Limited, London, England

[21] Appl. No.: 389,384

[22] Filed: Jun. 17, 1982

[30] Foreign Application Priority Data

Jun. 17, 1981 [GB] United Kingdom ............... 8118617

[51] Int. Cl.³ ........................................... G01N 21/88
[52] U.S. Cl. .................................... 356/430; 250/562; 356/380
[58] Field of Search ................. 356/71, 379, 380, 384, 356/385, 430; 250/562

[56] References Cited

U.S. PATENT DOCUMENTS 3,782,833 1/1974 Biggs et al. .......................... 356/380

FOREIGN PATENT DOCUMENTS 2310204 9/1974 Fed. Rep. of Germany ...... 356/385
159103 12/1980 Japan .................................... 356/385

*Primary Examiner*—R. A. Rosenberger
*Attorney, Agent, or Firm*—Kemon & Estabrook

[57] ABSTRACT

Figure 1:
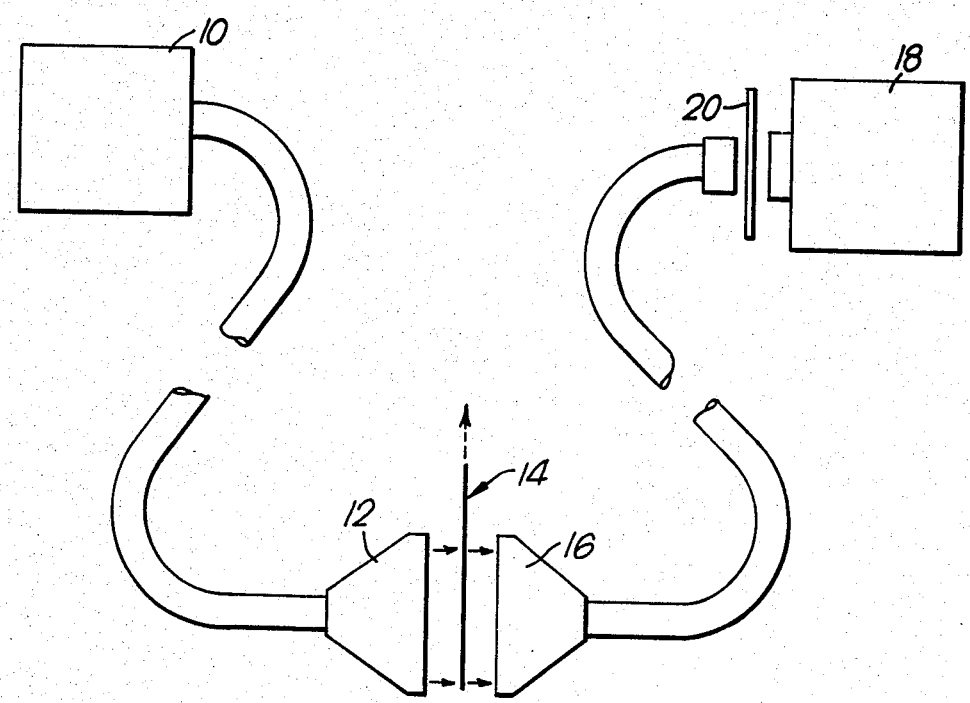

Apparatus for detecting missing areas or folded corners in sheets, for example banknotes (14), is disclosed. FIG. 1 shows a banknote (14) being scanned in a strip along one edge of the banknote. A strip light source 12 and a strip sensor 16 are disposed on opposite faces of the banknote which is caused to move perpendicularly to the light path between the source and sensor, and perpendicularly to the plane of the drawing. A photometer (18) responds to the total amount of light transmitted through the edge strip of the banknote (14) as the banknote is scanned. A filter (20) may be interposed in the light path to improve the sensitivity of the apparatus. The total amount of transmitted light detected by the photometer (18) is integrated over a period of the scan during which the intensity differs substantially from the mean level for an unflawed portion of the banknote. Integration is thus performed only over missing or folded areas of the banknote. It may also be limited to only the leading and trailing portions of the edge strip of the banknote, corresponding to the corners of the note.

In order to compensate for the passage of a skewed banknote passing through the apparatus, integration is inhibited over the said period whenever the intensity waveform from the photometer (18) is steeper than a predetermined gradient.

4 Claims, 14 Drawing Figures

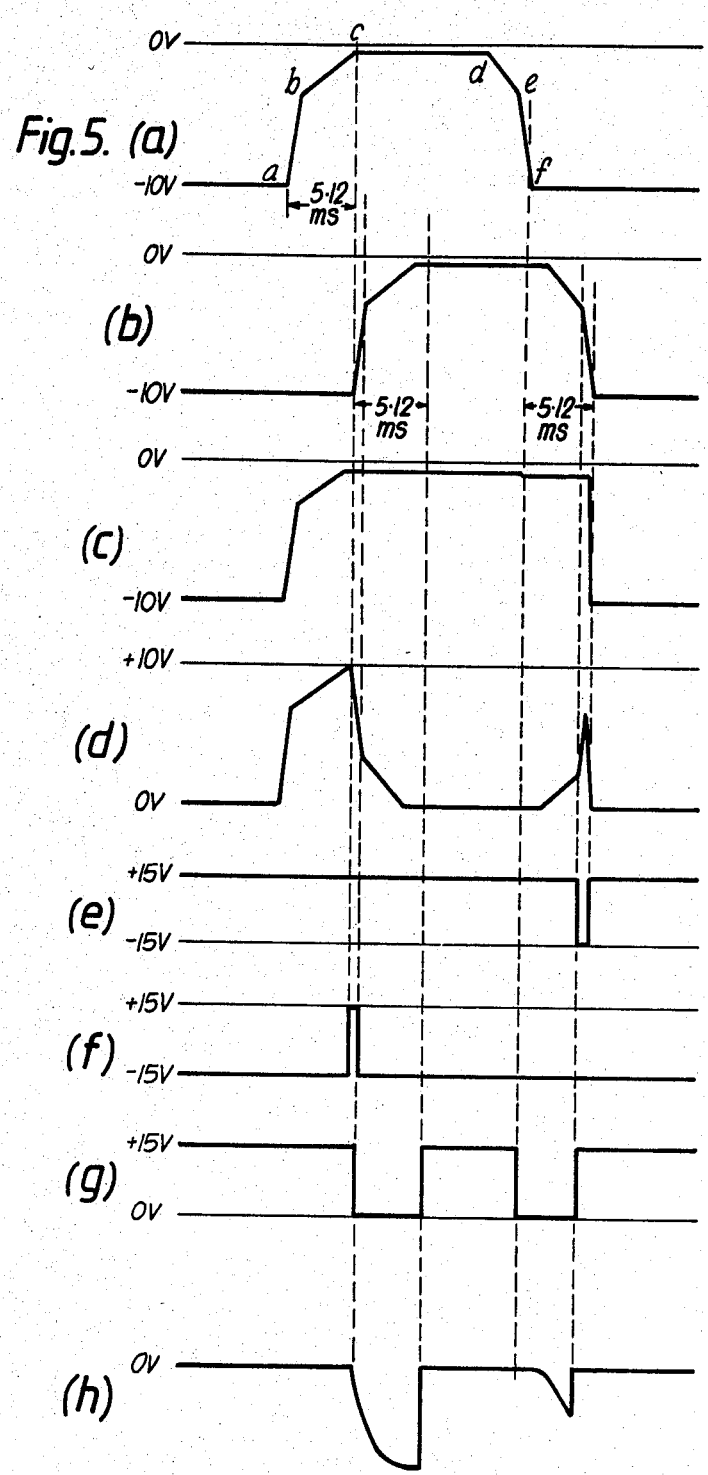

METHOD AND APPARATUS FOR INSPECTING SHEETS FOR FLAWS

This invention relates to the detection of flaws in sheets, for example banknotes. Frequently, it is required not only to detect missing areas or corner folds in banknotes, but also to measure the size of the missing area or corner fold and to reject the note if this size exceeds a predetermined value.

According to the present invention, a method of determining the size of a missing area (a hole, or a missing or folded corner, for example) in a sheet, comprises causing relative movement between the sheet and a sensing station having a strip light source on one side of the sheet and a strip sensor, aligned with the strip light source, on the other side of the sheet, the relative movement being perpendicular to the direction of the strip light source and strip sensor; detecting any difference between the sensor output and the output level of the sensor in the presence of an unflawed portion of the sheet, and integrating the said difference with respect to time over a given period. This given period may be the period during which the actual output level differs substantially from the mean level for the unflawed remainder of the sheet. Alternatively, this given period may be a predetermined time corresponding to the passage of a predetermined length of sheet from the leading edge or for the passage of a predetermined length preceding the trailing edge. If only missing or folded corners are of interest, it is only necessary to sense the marginal strips of the sheet or note.

The mean level may be obtained by integrating the sensor output while the sheet is scanned and dividing by the scanning time; this takes into account the degree of soiling. The effect of a missing area can be removed by inhibiting the integration when the sensor output is above a predetermined level. Alternatively, the required comparison may be made by delaying a waveform corresponding to the sensor output and then effecting a retrospective comparison of the value of this delayed waveform with the actual value of the waveform. In this way, an output value corresponding to a missing area or corner fold at the leading end of the sheet may be compared with a portion of the waveform which occurs after this leading end. Again, the mean level of sheet opacity across an unflawed portion of the strip is taken into account in considering the opacity of the leading end of the sheet. For the trailing end a sample of the mean value may be held for comparison with the opacity of the portion of the sheet preceding the trailing edge.

Skewed notes present a particular problem, in that during the passage of a skewed edge a waveform gives the appearance of a corner fold, with a long side in the direction of movement of the note. To overcome this problem, in the preferred method embodying the present invention, waveform portions having more than a predetermined slope are ignored, the integrating circuits being inhibited in the presence of such waveform portions.

Filters may be placed between the light source and the sheet, or between the sheet and the sensor, to increase the measurement accuracy, i.e. the sensitivity of the method to a missing area or corner fold.

The strip light source and the strip sensor may take the form of a light source and a plurality of fibre optics having their output ends arranged to form an illuminating strip, and a sensor having a plurality of fibre optics having their input ends arranged to form a sensing strip.

In order that the invention may be better understood, some examples of methods and apparatus embodying the invention will now be described with reference to the accompanying drawings.

In FIG. 1 of the drawings, there is shown a diagrammatic representation of the light source 10, a fibre optics coupling unit 12 converting the cylindrical light source output to a strip output illuminating a document 14, the light which passes through the document being collected by a fibre optic slit-to-spot converter 16 leading to a sensor 18 (photodiodes), by way of filter 20.

Figure 1A:
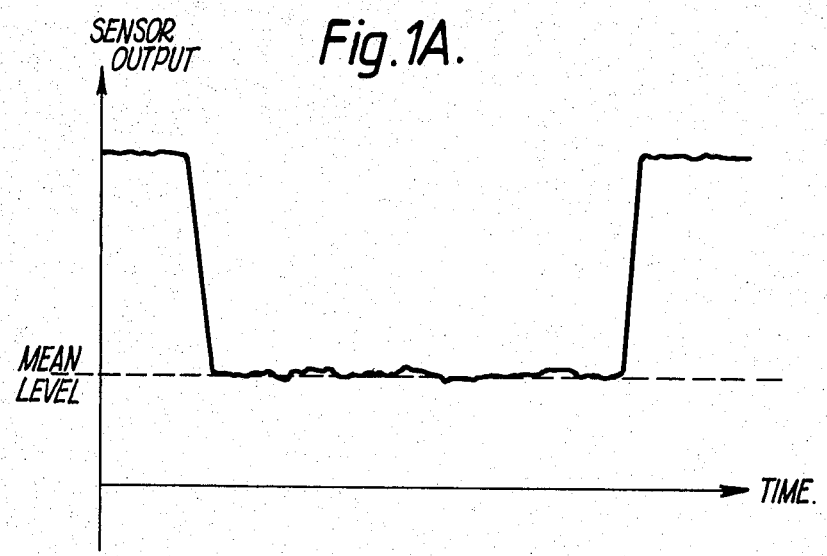
Figure 1B:
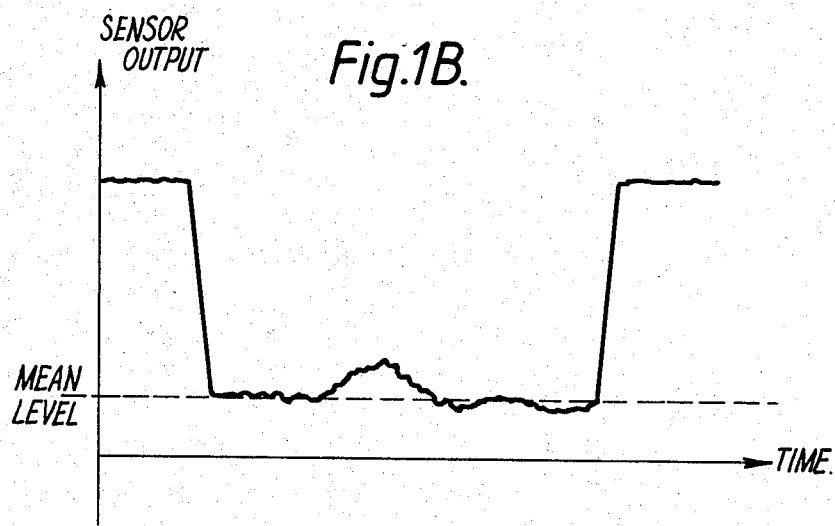
Figure 3:
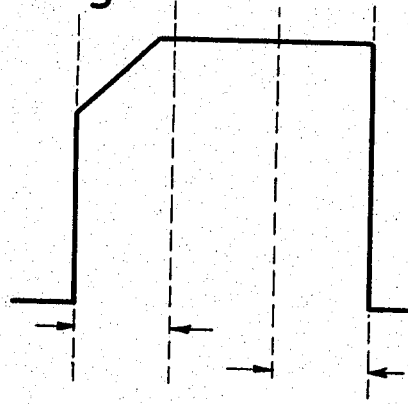

In the diagram shown, the document is transported lengthways in a direction perpendicular to the plane of the paper. The detector scans an edge strip along the length of the document. For a given document of known kind, for example a given banknote in mint condition, the sensor output will have a predetermined level with minor variations due to the pattern on the note, as shown schematically in FIG. 1A. If the note is soiled, as shown in FIG. 1B, this mean output will change. If there is a missing area, the sensor output waveform will exhibit an excursion during the passage of the missing area or corner fold past the detectors. If the flaw is a missing or folded corner, the abnormal sensor output level will occur at the leading end or at the trailing end of the note, as illustrated in FIG. 3. If desired, the area of the missing portion or of the corner fold can be measured by ascertaining the mean output level of the sensor in the absence of a missing area or corner fold, and comparing this mean level with the value when the missing area or corner fold passes the strip sensor, the difference value being integrated with respect to time.

If only corner folds are of interest, it is only necessary to scan two marginal portions of the note and to consider the sensor outputs only during an interval after the leading end passes the sensor and an interval immediately before the trailing end passes the sensor. The source and sensor overlap the edge of the note, to provide tolerance for lateral mis-registration.

Figure 2:
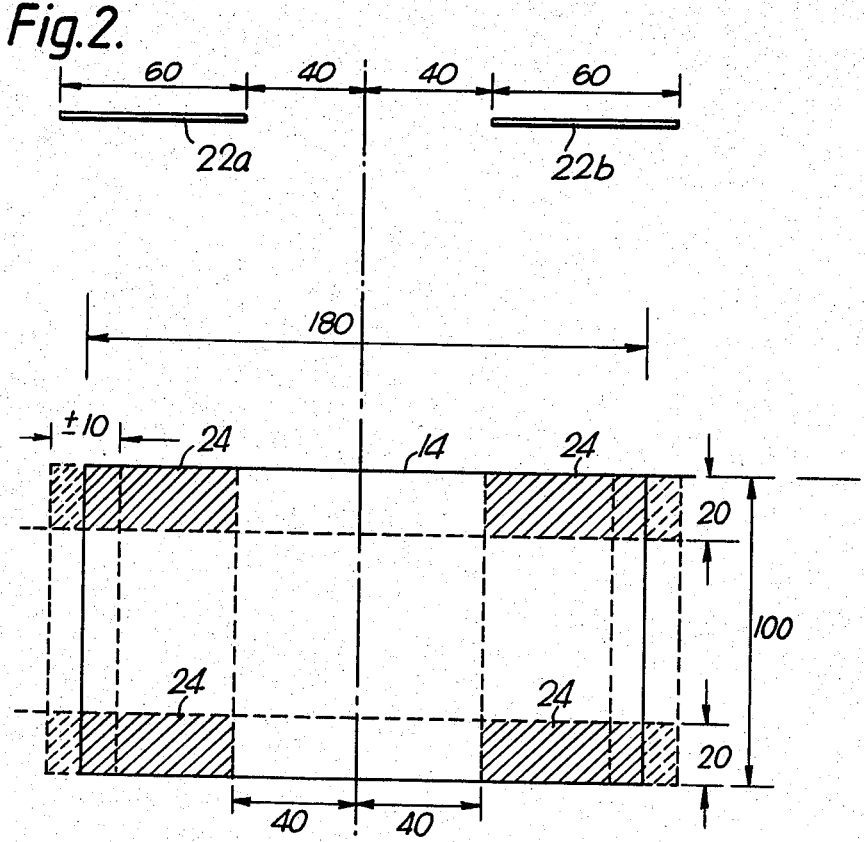

In FIG. 2, the optical slit portions of the sensor are shown at 22a and 22b and the areas of the note 14 which are considered are shown by 24.

The resultant waveform from one of the sensors when there is a corner fold (or tear) at the leading end is shown in FIG. 3; the waveform shown may be considered an electrical analogy of a note with a missing or folded corner.

If the flaw in a sheet or note is at the leading end, the difference between the sensor output corresponding to this flaw and a mean sensor output value, obtained in the presence of an unflawed portion of the note, is obtained by delaying the waveform and then comparing the delayed waveform corresponding to the corner fold with an actual output waveform. Similarly, a corner fold at the trailing end can be measured in area by comparing the sensor output value corresponding to the trailing-end corner-fold area with a preceding sensor level in the presence of the note or with the output of a sample-and-hold circuit, corresponding to the mean density of the note, if the documents are of different "heights", so that the position of the trailing edge cannot be forecast.

Figure 4:
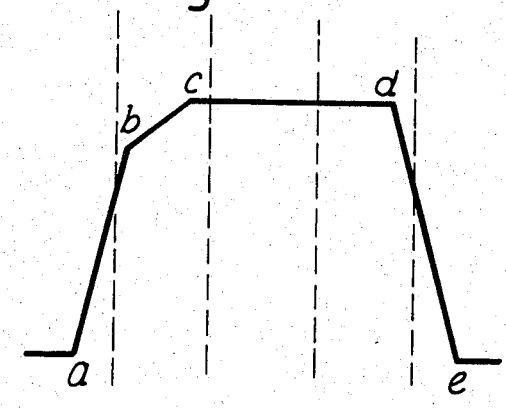

FIG. 4 illustrates the waveform obtained in the presence of a skewed note. It will be seen that portions a-b and d-e have slopes of very high value. A signal produced in the presence of a high slope value can be used to inhibit the operation of an integrator for the duration of the high slope values.

FIG. 5 shows waveforms obtained in one method embodying the present invention. In FIG. 5a the leading edge of the waveform a-b has such a high slope that it almost certainly represents the passage of the leading edge of a skewed note. The portion b-c of the waveform is of much smaller slope and is indicative of the presence of a corner fold or missing corner. Portion c-d is obtained during the period in which the sensor is fully covered by the moving note. Section d-e represents a smaller corner fold at the trailing edge of the note, and section e-f represents the passage of the skewed trailing edge past the sensor array.

As shown in FIG. 5b, the waveform derived from the sensor is delayed by a time equivalent to the distance of the boundaries of inspection from the leading or trailing edges of the document. FIG. 5c shows a waveform obtained by sampling and holding the undelayed waveform, thereafter sampling the delayed waveform and holding the sampled waveform value for the delayed period after the passage of the note.

Next, the height of the delayed waveform in the area between the leading edge and the first inspection boundary is subtracted from the stored height of the undelayed waveform at this boundary (FIG. 5d) and is integrated during this inspection time (FIG. 5h). However, integration does not take place during the portion of the delayed waveform corresponding to the skewed leading edge, the integrator being inhibited for this period by the output of a positive slope comparator (FIG. 5f).

Similarly, the height of the delayed waveform in the area between the second inspection boundary and the trailing edge is subtracted from the stored height of the delayed waveform at the second inspection boundary and is integrated during this inspection time. Again, integration is inhibited in the presence of an excessive slope; in this case, it is inhibited by the output of a negative slope comparator (FIG. 5e). The "integrator inhibit" waveform is shown in FIG. 5g.

The two integrated values shown in FIG. 5b are compared separately to a programmable threshold and a reject signal is produced if either value is above a limit.

This process takes place for each marginal strip of the note. In the example which is being described, the central area of the note was not inspected.

We found that the use of filters which limited the response of the optical system to the blue (shortwave) end of the spectrum improved the performance of the system.

I claim:

1. A method of determining the size of a missing or folded corner of a sheet, comprising:
    moving the sheet relative to a sensing station having a strip light source on one side of the sheet and a strip sensor, aligned with the strip light source, on the other side of the sheet, the strip light source and strip sensor being arranged in a direction perpendicular to the direction of relative movement;
    delaying a waveform corresponding to the sensor output and then effecting a comparison of the value of this delayed waveform with the value of the waveform corresponding to the sensor output, to detect any difference between the delayed waveform and the sensor output;
    and integrating the said difference with respect to time over a period which commences with the leading edge or terminates with the trailing edge of one of the waveforms.

2. A method in accordance with claim 1, wherein the difference between the delayed waveform and the sensor output for a trailing end of the sheet is detected by holding a sample of the sensor output for comparison with the delayed waveform in the period terminating with the trailing edge of the delayed waveform.

3. A method in accordance with claim 1, comprising placing a filter in the light path between the strip light source and the strip sensor, to increase the sensitivity of detection of a missing or folded corner.

4. A method in accordance with claim 1, wherein when the slope of the leading edge or the trailing edge of one of the waveforms which are being compared is greater than a predetermined slope, integration of the difference between the waveforms is prevented.

* * * * *